US006451893B1

(12) United States Patent
Tao

(10) Patent No.: US 6,451,893 B1
(45) Date of Patent: Sep. 17, 2002

(54) SOFT NITRILE ZINC OXIDE FREE MEDICAL GLOVES

(75) Inventor: Jian Tao, Reno, NV (US)

(73) Assignee: Microflex Corporation, Reno, NV (US)

(*) Notice: Subject to any disclaimer, the term of this patent is extended or adjusted under 35 U.S.C. 154(b) by 0 days.

(21) Appl. No.: 09/877,034

(22) Filed: Jun. 11, 2001

Related U.S. Application Data
(60) Provisional application No. 60/292,320, filed on May 22, 2001.

(51) Int. Cl.$^7$ .................................................. C08K 3/30
(52) U.S. Cl. ...................... 524/418; 524/419; 524/202; 524/343; 524/349; 524/83; 524/84; 524/95; 524/104; 524/435
(58) Field of Search ................................. 524/566, 572, 524/343, 418

(56) References Cited

U.S. PATENT DOCUMENTS

| | | | |
|---|---|---|---|
| 5,014,362 A | 5/1991 | Tillotson et al. ................ 2/168 |
| RE35,616 E | 9/1997 | Tillotson et al. ................ 2/168 |
| 5,872,173 A | * 2/1999 | Anand et al. ................ 524/494 |
| 5,881,387 A | 3/1999 | Merovitz et al. ............. 2/161.7 |
| 6,000,061 A | 12/1999 | Taneja et al. ................... 2/168 |
| 6,013,727 A | * 1/2000 | Dharmarajan et al. ......... 525/72 |
| 6,031,042 A | * 2/2000 | Lipinski ...................... 524/566 |

* cited by examiner

Primary Examiner—David W. Wu
Assistant Examiner—Rip A Lee
(74) Attorney, Agent, or Firm—Evan M. Kent, Esq.; Stewart L. Gitler, Esq.

(57) ABSTRACT

A new formulation for producing nitrile gloves has been developed. The resulting glove shows following outstanding characteristics: stress at six minutes greater than 50% of its initial value; ultimate tensile strength and elongation well above ASTM requirements; and much lower modulus than almost all the nitrile gloves currently commercially available. The unique formulation is zinc oxide free and is vulcanized from 5 to 60 minutes at temperatures ranging from 300° F to 400° F.

26 Claims, No Drawings

SOFT NITRILE ZINC OXIDE FREE MEDICAL GLOVES

Applicant claims the benefit of priority provisional patent application Serial No. 60/292,320, filed May 22, 2001.

BACKGROUND OF THE INVENTION

Natural rubber latex gloves provide excellent protection from numerous dangerous pathogens as well as many harsh chemicals. The natural rubber latex glove manufacturing industry mushroomed in early 1980s, especially in the Far East. However, soon after that, it was recognized that the inherent proteins of natural rubber latex would cause allergic reactions (Type I) to occur in certain people. In rare cases, the allergic reaction could be fatal. Therefore, for those people, alternatives, to natural rubber latex gloves, must be provided.

Although a series of synthetic materials including nitrile butadiene rubber (NBR), polychloroprene (CR), polyurethane (PU), polyisoprene (IR), polyvinyl chloride (vinyl, PVC), polyethylene (PE), etc. as well as many of their blends and copolymers have been used as alternatives to natural rubber latex, the overall performance and the cost of the alternatives are not quite satisfactory. Among the alternatives, nitrile butadiene rubber is the most popular one, an elastic glove at a reasonable cost.

U.S. Pat. No. 5,014,312, and Reissue Patent RE 35,616, both issued to Tillotson et al, cover nitrile butadiene rubber gloves. The patents address relaxation properties. The stress (or modulus) of the material under constant strain at six minutes should be less than 50% of its initial value. Most of the nitrile gloves currently commercially available have their relaxation property clustered about 40%, although that could be varying from 30~45%. Other gloves might have improved tensile strength, or elongation, or fewer additives that could cause Type IV allergic reactions (ZnO, etc.). None of them have displayed relaxations at six minutes that could exceed 50%.

Relaxation property is not an ASTM required quality control parameter for gloves. But together with modulus, another non-ASTM required quality control parameter for gloves; they can characterize the performance and the tactile sensation of, a glove. The higher the relaxation property, the better the glove will fit a hand's shape. Otherwise, the glove becomes loose after a while. But if high relaxation is combined with high modulus, the glove would quickly cause finger fatigue. Natural rubber latex gloves has a (relaxation>80%, and a 300% modulus (<2 MPa.), while nitrile butadiene rubber gloves show lower relaxation (typical 40%) and a much higher modulus at 300% (>7 Mpa).

Relaxation property is an intrinsic characteristic of material nature. Most nitrile butadiene latexes manufactured via emulsion polymerization would yield a relaxation of about 40%, as evidenced by the nitrile gloves currently available. This inherent property is predominantly caused by polymer chain structure, which would be determined by the polymerization mechanism. Different nitrile butadiene rubber vendors might have different controlling parameters and procedures, but their products have very little differentiation due to the fact that they all use emulsion polymerization for economic reasons.

Nitrile butadiene latexes, produced via polymerization mechanisms other than emulsification, namely for dipping. applications could have quite different structure, and thus different relaxation profiles, but there are no such products that are commercially available right now because of cost. Once the polymer chain structure has been predefined in the polymerization, there is little one can do to manipulate it. It is an objective of the invention to tune this parameter (relaxation) to above 50%. Meanwhile, the other mechanical properties must meet ASTM requirements.

SUMMARY OF THE INVENTION

This invention is a combination of an unique zinc oxide free formulation and selected vulcanization conditions that can be achieved economically with common production facilities. Produced are gloves that have a relaxation property, higher than 50%, and a low modulus (approximately 3 Mpa). The glove maintains decent ultimate tensile strength (>20 Mpa) and elongation (>500%). The glove is produced by a vulcanization process which lasts from 5 to 60 minutes at temperatures ranging from 300° F to 400° F. The tensile strength and elongation are well above the ASTM requirements for medical gloves. The current ASTM requirements are ASTM D412-92. Thanks to sufficient vulcanization, the films produced provide satisfactory protection from viral penetration. The tearing strength is also better because of the lower modulus.

DETAILED DESCRIPTION OF THE INVENTION

Compounding:

Carboxylated nitrile butadiene rubber undergoes two kinds of crosslinking in normal formulation and vulcanization. The first one is where carboxylated acid groups are linked to each other via a reaction with zinc oxide at room temperature. The second kind of crosslinking is where unsaturated butadiene blocks are crosslinked via a conventional sulfur system at elevated temperatures.

When zinc oxide is used, the relaxation property is not very sensitive to variation of zinc oxide content, although other mechanical properties (modulus, ultimate elongation and tensile strength) are favorable. One of our preferred formulations, produce films whose properties are comparable to those of natural rubber latex (300% modulus <2 Mpa, tensile strength >20 Mpa, and simultaneously elongation>500%). But, the relaxation at six minutes can not be higher than 45%. Therefore, zinc oxide was eliminated to prevent a performance reduction. The resulting formulation is tabulated as following:

| INGREDIENTS | PHR |
| --- | --- |
| Nitrile Butadiene Rubber | 100 |
| 2,2'-methylene-bis-(4-methyl-6-butylphenol) | 0.5 |
| zinc 2-mercaptobenzothiazole | 1.0 |
| zinc dibutyldithiocarbamate (BZ) | 1.0 |
| sulfur | 3.0 |
| potassium hydroxide | 1.0 |
| titanium dioxide | 0.5 |

Vulcanization Conditions:

Zinc oxide has been used as a primary activator for conventional sulfur vulcanization systems. By eliminating zinc oxide, higher temperatures were used during vulcanization. The films after leaching were dried at 260° F and then vulcanized at 300–400° F for 5–60 minutes. Conventionally, curing temperatures range between 2400° F and 285° F.

Mechanical Properties:

A couple of films obtained from the above formulation and vulcanization conditions show the following characteristics:

|        | Modulus at 300% (Mpa) | Ultimate Elongation (%) | Tensile Strength (Mpa) | % Initial Press at 6 min |
|--------|-----------------------|-------------------------|-------------------------|--------------------------|
| Film 1 | 3.11                  | 578                     | 23.93                   | 53.9                     |
| Film 2 | 3.20                  | 555                     | 21.03                   | 56.4                     |
| Film 3 | 3.83                  | 506                     | 21.36                   | 58.8                     |
| Film 4 | 3.77                  | 500                     | 18.99                   | 62.7                     |

As a result, we found zinc oxide free formulations and vulcanization conditions that yield higher relaxation properties and an improved soft glove. This combination shows a more balanced performance.

The zinc oxide free compound exhibited relaxation in the neighborhood of 55%. Powdering and/or leaching had no significant impact on glove properties. The formulations produce improved compounds and optimized vulcanization conditions (temperature and duration). The new formulations and procedures are easily realized economically under common nitrile-glove production lines. Depending on the desired applications, both powdered and powder free gloves could be produced in the same formula.

While the invention has been described with respect to a preferred embodiment, variations, modifications would be apparent to one of ordinary skill in the art without departing from the spirit of the invention.

What is claimed is:

1. A zinc oxide free elastomer formulation for a glove comprising:
    a nitrile butadiene rubber latex;
    sulfur;
    zinc di-n-butylthiocarbamate;
    2,2'-methylene-bis-(4-methyl-6-t-butylphenol); and
    zinc 2-mercaptobenzothiazole, wherein the sulfur is present in an amount of approximately 3.0 parts per 100 parts of the nitrile butadiene rubber.

2. The zinc oxide free elastomer formulation for a glove as claimed in claim 1, further comprising titanium dioxide present in an amount of approximately 0.5 parts per 100 parts of nitrile butadiene rubber.

3. The zinc oxide free elastomer formulation for a glove as claimed in claim 1, wherein the zinc di-n-butylthiocarbamate is present in an amount of approximately 1.0 parts per 100 parts of nitrile butadiene rubber.

4. The zinc oxide free elastomer formulation for a glove as claimed in claim 1, further comprising potassium hydroxide present in an amount of approximately 1.0 parts per 100 parts of nitrile butadiene rubber.

5. The zinc oxide free elastomer formulation for a glove as claimed in claim 1, wherein the zinc 2-mercaptobenzothiazole is present in an amount of approximately 1.0 parts per 100 parts of nitrile butadiene rubber.

6. The zinc oxide free elastomer formulation for a glove as claimed in claim 1, wherein the 2,2'-methylene-bis-(4-methyl-6-butylphenol) is present in an amount of approximately 0.5 parts per 100 parts of nitrile butadiene rubber.

7. The zinc oxide free elastomer formulation for a glove as claimed in claim 1, wherein the glove is vulcanized at a temperature ranging from 300–400° F.

8. The zinc oxide free elastomer formulation for a glove as claimed in claim 1, wherein the glove is vulcanized for from 5 to 60 minutes.

9. The zinc oxide free elastomer formulation for a glove as claimed in claim 1, wherein the glove is vulcanized at a temperature ranging from 300–400° F for from 5 to 60 minutes.

10. A zinc oxide free elastomer formulation for a glove comprising:
    approximately 100 parts of nitrile butadiene rubber;
    approximately 1.0 parts zinc di-n-butylthiocarbamate;
    approximately 3.0 parts sulfur;
    approximately 1.0 parts titanium dioxide;
    approximately 1.0 parts 2,2'-methylene-bis-(4-methyl-6-t-butylphenol);
    approximately 1.0 parts potassium hydroxide; and
    approximately 1.0 parts zinc 2-mercaptobenzo-thiazole.

11. The zinc oxide free elastomer formulation for a glove as claimed in claim 10, wherein the glove is vulcanized at a temperature ranging from 300–400° F.

12. The zinc oxide free elastomer formulation for a glove as claimed in claim 10, wherein the glove is vulcanized for from 5 to 60 minutes.

13. The zinc oxide free elastomer formulation for a glove as claimed in claim 10, wherein the glove is vulcanized at a temperature ranging from 300–400° F for from 5 to 60 minutes.

14. A zinc oxide free nitrile butadiene rubber for a glove which exhibits a relaxation property above 50%, wherein the glove is produced by a vulcanization process of heating the glove at a temperature ranging from 300–400° F for from 5 to 60 minutes.

15. A zinc oxide free nitrile butadiene rubber for a glove as claimed in claim 14, wherein the formulation further comprises sulfur.

16. A zinc oxide free nitrile butadiene rubber for a glove as claimed in claim 15, wherein the sulfur is present in an amount of approximately 3.0 parts per 100 parts of the nitrile butadiene.

17. A zinc oxide free nitrile butadiene rubber for a glove as claimed in claim 14, wherein the formulation further comprises zinc di-n-butylthiocarbamate.

18. A zinc oxide free nitrile butadiene rubber for a glove as claimed in claim 17, wherein the zinc dibutyldithiocarbamate is present in an amount of approximately 1.0 parts per 100 parts of nitrile butadiene rubber.

19. A zinc oxide free nitrile butadiene rubber for a glove as claimed in claim 14, wherein the formulation further comprises titanium dioxide.

20. A zinc oxide free nitrile butadiene rubber for a glove as claimed in claim 19, wherein the titanium dioxide is present in an amount of approximately 0.5 parts per 100 parts of nitrile butadiene rubber.

21. A zinc oxide free nitrile butadiene rubber for a glove as claimed in claim 14, wherein the formulation further comprises zinc 2-mercaptobenzothiazole.

22. A zinc oxide free nitrile butadiene rubber for a glove as claimed in claim 21, wherein the zinc 2-mercaptobenzothiazole is present in an amount of approximately 1.0 parts per 100 parts of nitrile butadiene rubber.

23. A zinc oxide free nitrile butadiene rubber for a glove as claimed in claim 14, wherein the formulation further comprises 2,2'-methylene-bis-(4-methyl-6-t-butylphenol).

24. A zinc oxide free nitrile butadiene rubber for a glove as claimed in claim 23, wherein the 2,2'-methylene-bis-(4-methyl-6-t-butylphenol) is present in an amount of approximately 0.5 parts per 100 parts of nitrile butadiene rubber.

25. A zinc oxide free nitrile butadiene rubber for a glove as claimed in claim 14, wherein the formulation further comprises potassium hydroxide.

26. A zinc oxide free nitrile butadiene rubber for a glove as claimed in claim 25, wherein the potassium hydroxide is present in an amount of approximately 1.0 parts per 100 parts of nitrile butadiene rubber.

* * * * *

UNITED STATES PATENT AND TRADEMARK OFFICE
CERTIFICATE OF CORRECTION

PATENT NO.   : 6,451,893 B1
DATED        : September 17, 2002
INVENTOR(S)  : Tao It is certified that error appears in the above-identified patent and that said Letters Patent is hereby corrected as shown below:

<u>Column 2,</u>
Line 67, kindly replaces "2400° F" with -- 240° F --.

Signed and Sealed this

Fourth Day of February, 2003

JAMES E. ROGAN
*Director of the United States Patent and Trademark Office*